United States Patent [19]
Athanikar

[11] Patent Number: 5,834,002
[45] Date of Patent: Nov. 10, 1998

[54] CHEWING GUM CONTAINING COLLOIDAL BISMUTH SUBCITRATE

[75] Inventor: Narayan K. Athanikar, Irvine, Calif.

[73] Assignee: Josman Laboratories, Inc., Orange, Calif.

[21] Appl. No.: 741,781

[22] Filed: Nov. 1, 1996

Related U.S. Application Data

[63] Continuation-in-part of Ser. No. 385,060, Feb. 7, 1995, abandoned.

[30] Foreign Application Priority Data

May 2, 1994 [JP] Japan ................................. 6-93518

[51] Int. Cl.$^6$ ..................................... A61K 9/68
[52] U.S. Cl. ........................... 424/440; 424/441; 424/48; 424/52
[58] Field of Search ................................ 424/440, 48, 49, 424/401, 52, 131; 514/25; 426/3

[56] References Cited

U.S. PATENT DOCUMENTS

| | | | |
|---|---|---|---|
| 3,011,949 | 12/1961 | Bilotti | 167/82 |
| 3,352,689 | 11/1967 | Bilotti | 99/135 |
| 3,824,006 | 7/1974 | Voit | 351/106 |
| 3,929,449 | 12/1975 | Hedrich | 71/82 |
| 3,943,258 | 3/1976 | Bahoshy et al. | 426/3 |
| 3,973,041 | 8/1976 | DuRoss | 426/3 |
| 4,055,655 | 10/1977 | Maurer et al. | 424/290 |
| 4,153,685 | 5/1979 | Serfontein . | |
| 4,180,473 | 12/1979 | Maurer et al. | 252/102 |
| 4,208,431 | 6/1980 | Friello et al. | 426/3 |
| 4,217,368 | 8/1980 | Witzel et al. | 426/5 |
| 4,514,421 | 4/1985 | Herschler | 514/711 |
| 4,652,444 | 3/1987 | Maurer | 424/49 |
| 4,670,245 | 6/1987 | Vasquez . | |
| 4,680,309 | 7/1987 | Maurer | 515/503 |
| 4,801,454 | 1/1989 | Coveney | 424/131 |
| 4,801,608 | 1/1989 | Bos et al. | 515/503 |
| 4,822,597 | 4/1989 | Faust et al. | 424/40 |
| 4,879,116 | 11/1989 | Fox et al. | 424/682 |
| 4,940,695 | 7/1990 | Coveney et al. . | |
| 4,956,386 | 9/1990 | McLoughlin et al. | 514/503 |
| 4,965,382 | 10/1990 | Furlan | 556/79 |
| 4,975,270 | 12/1990 | Kehoe | 424/40 |
| 5,013,560 | 5/1991 | Stentz et al. . | |
| 5,017,367 | 5/1991 | Stojkoski | 424/63 |
| 5,093,342 | 3/1992 | Tomoi et al. | 514/328 |
| 5,192,752 | 3/1993 | Chapura | 514/152 |
| 5,256,684 | 10/1993 | Marshall | 514/398 |
| 5,264,222 | 11/1993 | Groenendaal et al. | 424/451 |
| 5,286,492 | 2/1994 | Dettmar | 424/458 |
| 5,294,433 | 3/1994 | Singer | 424/52 |
| 5,352,679 | 10/1994 | Ferrieri et al. | 514/279 |
| 5,372,815 | 12/1994 | Hodutu | 424/401 |
| 5,385,739 | 1/1995 | Debregeas et al. | 424/494 |
| 5,403,830 | 4/1995 | Place | 514/184 |
| 5,425,948 | 6/1995 | Olivieri | 424/401 |
| 5,466,681 | 11/1995 | Krivan et al. | 514/54 |
| 5,476,669 | 12/1995 | Borody | 424/653 |
| 5,514,660 | 5/1996 | Zopf | 514/25 |
| 5,536,510 | 7/1996 | Tyrpin et al. | 426/4 |
| 5,601,848 | 2/1997 | Marshall | 424/563 |

FOREIGN PATENT DOCUMENTS

| | | |
|---|---|---|
| 0 075 992 | 9/1982 | European Pat. Off. . |
| 0075992 | 4/1983 | European Pat. Off. . |
| 0403048 | 6/1989 | European Pat. Off. . |
| 0367484 | 5/1990 | European Pat. Off. . |
| 0375063 | 6/1990 | European Pat. Off. . |
| 0437294 | 7/1991 | European Pat. Off. . |
| 2012187 | 12/1971 | Germany . |
| A-7-96974 | 1/1996 | Japan . |
| 91/03241 | 3/1991 | WIPO . |
| 92/01457 | 2/1992 | WIPO . |

OTHER PUBLICATIONS

Beil et al., "Studies on the Mechanism of Action of Colloidal Bismuth Subcitrate," *Pharmacology* 47:135–140 (1993).

Beil et al., "Studies on the Mechanism of Action of Colloidal Bismuth Subcitrate," *Pharmacology* 47:141–144 (1993).

Hosking et al., "Duodenal Ulcer Healing by Eradication of Helicobacter Pylori Without Anti–acid Treatment: Randomised Controlled Trial," *The Lancet* 343:508–510 (1994).

Lee, "The Mode of Action of Colloidal Bismuth Subcitrate," *Scand. J. Gastroenterol* 26(185):1–6 (1991).

Norfleet, "Helicobacter Halitosis", *J. Clin. Gastroenterol*, vol. 16, No. 3, 1993.

Rosenberg et al., "Day–Long Reduction of Oral Malodor by a Two–Phase Oil: Water Mouthrinse as Compared to Chlorhexidine and Placebo Rinses", *J. Periodontol*, 63(1): 39–43 (1982).

Tiomny et al., "Halitosis and Helicobacter Pylori", *J. Clin. Gastroenterol* 15(3):236–237 (1992).

Bosy et al., "Relationship of Oral Malodor to Periodontitus: Evidence of Independence in Discrete Subpopulations", *J. Periodontol*, 65(1):37–46 (1992).

De Boever et al., "Assessing the Contribution of Anaerobic Microflora of the Tongue to Oral Malodor", *JADA*, vol. 126, Oct., 1995.

Kleinberg et al., "Salivary and Metabolic Factors Involved in Oral Malodor Formation", *J. Periodontol*, 63(9): 768–775 (1992).

1994 Annual Report for Applied Microbiology, Inc.; distributed with notice of Annual Shareholders Meeting which was mailed Feb., 1995.

(List continued on next page.)

*Primary Examiner*—Thurman K. Page
*Assistant Examiner*—D. Faulkner
*Attorney, Agent, or Firm*—Brinks Hofer Gilson & Lione

[57] ABSTRACT

The invention provides a chewing gum composition containing a water soluble bulk portion, a water insoluble chewing gum base portion, a flavoring agent, and bismuth-containing compounds. The invention provides a bismuth-containing gum which when chewed multiple times per day, over the period of two weeks, is effective in reducing peptic ulcers by eradicating *H. pylori*. The chewing gum is also effective in eliminating forms of halitosis. The chewing gum does not have undesirable side effects, unpleasant taste and poor chewing characteristics.

32 Claims, No Drawings

OTHER PUBLICATIONS

Axton, A.T.R., Campyobacter pylori—Therapy Review, Scand. J. Gastroenterol., 1989, 24 (suppl 160), 35–38.

Benet, L.Z., Safety and Pharmacokinetics: Colloidal Bismuth Subcitrate, Scand. J. Gasstroenterol., 1991, 26 (Suppl 185), 29–35.

Boyd, E.J.S. et al., Recurrent ulcer disease, *Gastroenterology Clinics of America. Helicobacter pylori Infection*, Dooley CP, Cohen, H. Guest Editors, vol. 22, No. 1, pp. 14–42, Mar. 1993.

Desai, H.G. et al., Dental Plaque: A Permanent Reservoir of Helicobacter Pylori?, Scand. J. Gastroenterol., 1991, 26, 1205–1208.

Dobrilla, G. et al., Influence of ulcer healing agents on ulcer relapse after discontinuation of acute treatment: a pooled estimate of controlled clinical trials, Gut., 1988, 29, 181–187.

Goh, K.L. et al., Helicobacter pylori Infection and Non–Ulcer Dyspepsia: The Effect of Treatment with Colloidal Bismuth Subcitrate, Scand. J. Gastroenterol., 1991, 26, 1123–1131.

Goodwin, C.S. et al., The minimum inhibitory and bactericidal concentrations of antibiotics and anti–ulcer agents against Campylobacter pyloridis, J. Antimicrobial Chemotherapy (1986) 17, 309–314.

Jensen, L. et al., Chewing gum and lozenges as delivery systems for noscapine, Acta Pharm. Nord. 3(4):219–222 (1991).

Jones, D.B. et al., Acid suppression in duodenal ulcer: a meta–analysis to define optimal dosing with antisecretory drugs, Gut. 1987, 28, 1120–1127.

Lambert, I., The Lancet, vol. 341, Apr. 1993, p. 957.

Lambert, J.R., Clinical Indications and Efficacy of Colloidal Bismuth Subcitrate, Scand. J. Gastroenterol., 1991, 26 (suppl 185), 13–21.

Lambert, T. et al., Susceptibility of Campylobacter pyloridis to 20 Antimicrobial Agents, Antimicrobial Agents and Chemotherapy, Sep. 1986, pp. 510–511.

Lashner, B.A. et al., Testing Nicotine Gum for Ulcerative Colitis Patients, Digestive Diseases and Sciences, vol. 35, No. 7 (Jul. 1990), pp. 827–832.

Lees, V.C. et al., A freeze–injured skin graft model for the quantitative study of basic fibroblast growth factor and other promoters of angiogenesis in wound healing, British Journal of Plastic Surgery (1994), 47, 349–359.

Marshall, Treatment Strategies for Helicobacter Pylori Infection, *Gastroenterology Clinics of America. Helicobacter pylori Infection*, Dooley CP, Cohen, H. Guest Editors. vol. 22, No. 1, pp. 186–195.

Matuszewska, B. et al., Acidic Fibroblast Growth Factor: Evaluation of Topical Formulations in a Diabetic Mouse Wound Healing Model, Pharmaceutical Research, vol. 11, No. 1, 1994, pp. 65–71.

McNulty, C. et al., Susecptibility of Clinical Isolates of Campylobacter pyloridis to 11 Antimicrobial Agents, Antimicrobial Agents and Chemotherapy, vol. 28, No. 6, Dec. 1985, pp. 837–838.

Mustofa et al., Pharmacokinetics of metronidazole in saliva, International Journal of Clinical Pharmacology, Therapy, and Toxicology, Dec. 1991, 29(12):474–478.

Nguyen, A. et al., Detection of Helicobacter pylori in Dental Plaque by Reverse Transcription–Polymerase Chain Reaction, J. Clin. Microbiol., vol. 31, No. 4, pp. 783–787 (1993).

Wagner, S. et al., Bismuth subsalicylate in the treatment of $H_2$ blocker resistant duodenal ulcers: role of Helicobacter pylori, Gut., 1992, 33, 179–183.

Wieriks, J. et al., Pharmacological Properties of Colloidal Bismuth Subcitrate (CBS, DE–NOL®), Scand. J. Gastroenterol., 1982, 17, Suppl 80, 11–16.

Wormsley, K., Relapse of duodenoal ulcer, British Medical Journal, vol. 293, 1986, p. 1501.

Wu, L. et al., Platelet–derived Growth Factor–BB Accelerates Wound Closure in a New Mesentery Culture Model Without Macrophages, Annals of Plastic Surgery, vol. 33, No. 2, Aug. 1994, p. 155.

Konturek et al., Scandanavian Journal of Gastroenterology 21 (Suppl. 122) :6–10 (1986).

Konturek et al., Digestion 37 (Suppl. 2) :8–15 (1987).

Lee et al., Lancet 1:1299–1301 (1985).

Lee, S.P., Scandinavian Journal of Gastroenterology 26 (Supp 1985) :1–6 (1991).

Logan et al., The Lancet 338:1249–1252 (1991).

O'Connor et al., Gut 30:436–442 (1989).

Olsson et al., The Lancet 341:956–957 (1993).

Parsonnet, J., Gastroenterology Clinics of North America 22(1) :89–104 (1993).

Recavarren–Arce et al., Scandanavian Journal of Gastroenterology 26 (Suppl. 181) :51–57 (1991).

Reed et al., Iarc Scientific Publications 105:139–142 (1991).

Schorah et al., Clin Nutr 53:287S–293S (1991).

Sobala et al., Gut 32:1415–1418 (1991).

Sobala et al., Gastroenterology 97:357–363 (1989).

Abraham et al., Indian Journal of Gastroenterology 9(4):265–269 (1990).

Bianchi et al., The British Society of Gastroenterology 25:A565 (1984).

Bianchi et al., Digestion 37 (Suppl. 2) :47–52 (1987).

Bianchi et al., The Lancet 2:698 (1984).

Borody et al., Gastroenterology 102 (4, part 2) :A44 (1992).

Graham et al., Gastroenterology 102:493–496 (1992).

CHEWING GUM CONTAINING COLLOIDAL BISMUTH SUBCITRATE

This application is a C-I-P of Ser. No. 08/385,060 filed Feb. 07, 1995 now abandoned.

BACKGROUND OF THE INVENTION

This invention relates to chewing gum compositions containing active ingredients. More particularly, this invention relates to producing chewing gums that contain compounds for treating ulcers and halitosis.

Chewing gum compositions, typically, include a water soluble bulk portion, a water insoluble chewing gum base portion and water insoluble flavoring agents. Also, chewing gum compositions can be formulated to provide the delivery of active agents. These active agents may be a variety of breath fresheners, or medicaments, such as laxatives, aspirin or nicotine. Delivering these medicaments through a chewing gum vehicle is desirable for people who have difficulty swallowing pills. Also, the bad taste of some of the agents may be disguised by stronger flavoring agents in the chewing gum, which may make gum a suitable vehicle for delivery of certain medicines. Moreover, some medicines may be absorbed directly into the bloodstream through the tissue lining the mouth, making the medicine more readily available than if absorbed through the gastrointestinal walls. Accordingly, many people can benefit from new discoveries of how to effectively deliver active ingredients through a chewing gum formulation.

Unfortunately, many active ingredients are not suitable for administration through a chewing gum for a variety of reasons. A chewing gum cannot be effective if it has unpleasant medicinal taste, causes discoloration in the user's mouth, or the active ingredient causes poor chewing characteristics. A chewing gum cannot be effective if the active ingredient is not readily released from the gum, and thus, not delivered either into the mouth or the stomach where it can be absorbed or act topically. For this reason, many active ingredients may be effectively delivered by chewable tablets, or swallowable tablets, but not by chewing gum.

Recent discoveries have associated bacterial infection in the causation of peptic ulcer disease. The bacterium found to be associated with peptic ulcers has been identified as *Helicobacter pylori*. Excessive gastric acidity and mental stress are no longer thought to be the major pathophysiological reasons for the occurrence of peptic ulcers. Thus, questions regarding the previously established paradigms of and approaches for ulcer treatment and healing processes have been raised.

Previously, ulcers were treated by suppressing secretion of acid in the stomach. H2-receptor blockers, such as cimetidine (Tagamet®) and Ranitidine (Zantac®), suppress acid secretion and have been used to treat and heal duodenal ulcers. However, these H2-receptor blockers do not eliminate the *Helicobacter pylori* bacteria ("*H. pylori*"). These drugs do not reverse the tendency for ulcers to form.

For many years bismuth compounds have been used in swallowable tablet form and liquid form for treating ulcers. The therapeutic efficacy of bismuth compounds such as colloidal bismuth subcitrate, CBS, (also known as tripotassium dicitrato bismuthate), in healing duodenal ulcers and lowering relapse rates is attributed to its specific antibacterial activity against *H. pylori*. However, using bismuth compounds alone, *H. pylori* eradication rates of about 10 to 40% has been reported. Also, patients would suffer a relapse of ulcers after discontinuing taking the bismuth compounds.

Even though, as a single agent, CBS is significantly more effective in eradicating *H. pylori* than many other antibiotics, multiple therapies of bismuth compounds combined with other antibiotics have been reported to result in more than a 95% eradication rate for *H. pylori* and reduced ulcer relapse rate to less than 10% during a twelve-month follow-up period. For example, one such common triple therapy, comprised of CBS, amoxicillin and metronidazole, has been reported to have a high rate of effectiveness. However, it would be desirable to achieve such effectiveness in eradicating *H. pylori* with simple single agent therapies. No such single agent heretofore has been shown to be effective.

SUMMARY OF THE INVENTION

The present invention, therefore, is related to development of a chewing gum formulation to effectively eradicate *H. pylori* colonies without the need for combination antibiotic therapies. This invention is related to a chewing gum formulation containing a water soluble bulk portion, a water insoluble chewing gum base portion, a flavoring agent, and compounds selected from the group consisting of colloidal bismuth subcitrate, bismuth citrate, bismuth subcitrate, bismuth salicylate, bismuth subsalicylate, bismuth subnitrate, bismuth subcarbonate, bismuth tartrate, bismuth subgallate, bismuth aluminate, and combinations thereof. This chewing gum has been found to eradicate or reduce *H. pylori* in reservoirs in the oral cavity and at the cite of infection and ulceration in the gastric mucosa. The invention further provides for a method of treating *H. pylori* infection by the administration of a chewing gum containing an amount of bismuth in a bismuth-containing compound equivalent to between about 10 and 200 milligrams of colloidal bismuth subcitrate. The invention further provides for the method of treating halitosis by the administration of a chewing gum containing bismuth compounds.

DETAILED DESCRIPTION OF THE INVENTION

In general, chewing gum compositions include a water soluble bulk portion, a water insoluble chewing gum base portion and, typically, water insoluble flavoring agents. The water soluble portion dissipates with a portion of the flavoring agents over a period of time during chewing. The gum base portion is retained in the mouth throughout the chewing process.

The insoluble gum base generally includes elastomers, resins, fats, oils, waxes, softeners and inorganic fillers. The elastomers may include polyisobutylene, isobutylene-isoprene copolymer, styrene butadiene rubber and natural latexes such as chicle. The resins may include polyvinyl acetate and terpene resins. Low molecular weight polyvinyl acetate is a preferred resin. Fats and oils may include animal fats such as lard and tallow, vegetable oils such as soybean and cottonseed oils, hydrogenated and partially hydrogenated vegetable oils, and cocoa butter. Commonly used waxes include petroleum waxes such as paraffin and microcrystalline wax, natural waxes such as paraffin and microcrystalline wax, natural waxes such as beeswax, candellia, carnauba and polyethylene wax. Preferably, the waxes have a melting point between 95° F. and 240° F.

The gum base typically also includes a filler component such as calcium carbonate, magnesium carbonate, talc, dicalcium phosphate and the like; elastomers, including glycerol monostearate and glycerol triacetate; and optional ingredients such as antioxidants, colors and emulsifiers. The gum base constitutes between 5 and 95% by weight of the chewing gum composition, more typically 10–50% by weight of the chewing gum, and commonly 25–35% by weight of the chewing gum.

The water soluble portion of the chewing gum may include softeners, bulk sweeteners, high intensity sweeteners and combinations thereof Softeners are added to the chewing gum in order to optimize the chewability and mouth feel of the gum. The softeners, which are also known as plasticizers or plasticizing agents, generally constitute between about 0.5–15% by weight of the chewing gum. The softeners may include glycerin, lecithin, and combinations thereof The softeners may also include aqueous sweetener solutions such as those containing sorbitol, hydrogenated starch hydrolysates, corn syrup and combinations thereof.

Bulk sweeteners constitute between 20–80% by weight of the chewing gum and may include both sugar and sugarless sweeteners and components. Sugar sweeteners may include saccharide containing components including but not limited to sucrose, dextrose, maltose, dextrin, dried invert sugar, fructose levulose, galactose, corn syrup solids, and the like, alone or in combination. Sugarless sweeteners include components with sweetening characteristics but are devoid of the commonly known sugars. Sugarless sweeteners include but are not limited to sugar alcohols such as sorbitol, mannitol, xylitol, hydrogenated, starch hydrolysates, maltitol, and the like, alone or in combination.

High intensity sweeteners may also be present. These may include but are not limited to sucralose, aspartame, salts of acesulfame, alitame, saccharin and its salts, cyclamic acid and its salts, dihydrochalcones, thaumatin, monellin, and the like, alone or in combination.

Combinations of sugar and/or sugarless sweeteners may be used in chewing gum. The sweetener may also function in the chewing gun in whole or in part as a water soluble bulking agent. Additionally, the softener may also provide additional sweetness such as with aqueous sugar or alditol solutions.

One or more flavoring agents are generally present in the chewing gum in an amount within the range of about 0.1–10% by weight of the chewing gum, preferably between about 0.5–3% by weight of the chewing gum. The flavoring agents may include essential oils, synthetic flavors or mixtures thereof including but not limited to oils derived from plants and fruits such as citrus oils, fruit essences, peppermint oil, spearmint oil, other mint oils, clove oil, oil of wintergreen, anise and the like. Artificial flavoring agents and components may also be used. Natural and artificial flavoring agents may be combined in any sensorally acceptable fashion. All such flavors and flavor blends are contemplated by the present invention.

Optional ingredients such as colors, such as titanium dioxide and the like, emulsifiers and pharmaceutical agents may also be included in chewing gum.

The active pharmaceutical agents in this chewing gum formulation of this invention include non-H2 antagonist bismuth compounds. These bismuth compounds include colloidal bismuth subcitrate (CBS), bismuth citrate, bismuth subcitrate, bismuth salicylate, bismuth subsalicylate, bismuth subnitrate, bismuth subcarbonate, bismuth tartrate, bismuth subgallate, and bismuth aluminate.

Preferably, the bismuth compound is selected from Colloidal Bismuth Subcitrate (CBS), bismuth subcitrate, bismuth subsalicylate and their combination. Most preferably, the bismuth compound is Colloidal Bismuth Subcitrate (CBS). The structural formula of CBS is:

[Bi(OH)$_3$]$_3$BiC$_6$H$_6$O$_7$ (1,2,3-PROPANETRICARBONIC ACID, 2-HYDROXY, BISMUTH(3T)POTASSIUM; CAS#57644-54-9

Colloidal bismuth subcitrate and other bismuth compounds may be coated, micro-encapsulated, or agglomerated before incorporating in the chewing gum formulation to further cause the slow dissolution and sustained concentration of the compounds in the saliva. The polymers used for coating or encapsulation may include methylcellulose, carboxymethylcellulose, hydroxy-propylmethylcellulose, ethylcellulose, carbowax, polyethyleneglycols, acrylic polymers, to name a few. For example, CBS can be coated with a coating solution containing hydroxy-propylcellulose and polyethylene glycol in hydro-alcoholic solvent employing a fluid-bed coating equipment. The coated CBS particles should be assayed for CBS content and dissolution characteristics.

It is preferred that the chewing gum formulation containing bismuth compounds be capable of releasing the drug in a precise and reproducible fashion during a fifteen-minute chewing time. Preparing the bismuth compound using any of the above techniques may achieve such uniform release.

The chewing gum formulations may also include anti-plaque agents. The anti-plaque agents further contribute to improved efficacy by breaking down the plaque and exposing the *H. pylori* bacterial colonies to the anti-bacterial agents. Anti-plaque agents include, but are not limited to, glucanase anhydroglucosidase, glucose oxidase, calcium kaolin, silicone oil, sanguinarine, and the like.

Optionally, an antibiotic, such as metronidazole, can be added to the chewing gum formulation to broaden the anti-microbial activity against *H. pylori*. However, a preferred form of the chewing gum comprises an active pharmaceutical agent that consists essentially of a bismuth compound selected from the group consisting of colloidal bismuth subcitrate (CBS), bismuth citrate, bismuth subcitrate, bismuth salicylate, bismuth subsalicylate, bismuth subnitrate, bismuth subcarbonate, bismuth tartrate, bismuth subgallate, and bismuth aluminate.

Chewing gum is generally manufactured by sequentially adding the various chewing gum ingredients to any commercially available mixer known in the art. Generally, the ingredients are mixed by first melting the gum base and adding it to the running mixer. The gum base may alternatively be melted in the mixer. Color and emulsifiers can be added at this time. A softener such as glycerin can be added next along with syrup and part of the bulk portion. Further parts of the bulk portion may then be added to the mixer. The flavoring agent, pharmaceutical agent, and other optional ingredients of this ilk, are typically added with the final part of the bulk portion. The entire mixing process typically takes from five to fifteen minutes, although longer mixing times are sometimes required. Those skilled in the art will recognize that variations of this mixing procedure, or other mixing procedures, may be followed.

After the ingredients have been thoroughly mixed, the gum mass is discharged from the mixer and shaped into the desired form such as by rolling into sheets and cutting into sticks, extruding into chunks, or casting into pellets. Pellet or ball gum is prepared as conventional chewing gum, but formed either into pellets that are pillow-shaped or into balls. The pellets/balls can then be coated or panned by conventional panning techniques to make a unique sugar-coated pellet gum. Conventional panning procedures generally apply a liquid coating to a pellet, which is then solidified, usually by drying the coating. The hard-shell coating layer is built up by successive coating and drying steps.

Conventional panning procedures generally coat with sucrose, but recent advances in panning have allowed the use of other carbohydrate materials to be used in the place of sucrose, yet still obtain a hard-shell coating. Some of these components include, but are not limited to, dextrose, maltose, xylitol, lactitol, palatinit and other new alditols or a combination thereof These materials may be blended with panning modifiers including, but not limited to, gum arabic, maltodextrins, corn syrup, gelatin, cellulose type materials like carboxymethyl cellulose or hydroxymethyl cellulose, starch and modified starches, vegetable gums like alginates, locust bean gum, guar gum, and gum tragacanth, insoluble carbonates like calcium carbonate or magnesium carbonate, and talc. Antitack agents may also be added as panning modifiers, which allow the use of a variety of carbohydrates and sugar alcohols to be used in the development of new panned or coated gum products. Flavors may also be added with the sugar coating and with the bulk sweetener to yield unique product characteristics.

The chewing gum formulation of the present invention is superior to conventional therapy for treating ulcers. It turns out that the conventional bismuth therapy was shown to be only somewhat effective in eliminating *H. pylori* from the gastric mucosa, but had no effect on the *H. pylori* colonies in dental plaque. Colloidal bismuth subcitrate (CBS), an effective agent against *H. pylori,* however, is not absorbed significantly from the gastrointestinal tract, and therefore produces insufficient salivary concentrations through systemic recycling to affect *H. pylori* in the mouth. This continued presence of *H. pylori* in the dental plaque, and possibly the throat and esophagus, raises the question of whether the relapse of ulcers was inevitable with conventional bismuth therapy.

Multiple therapies of bismuth compounds combined with other antibiotics have been found to be superior to conventional bismuth therapy. Typical combinations include bismuth subsalicylate, metronidazole and amoxicillin or tetracycline. One possible explanation for the observed clinical efficacy of the antibiotic and bismuth combination that has not been advanced by the scientific community is that the metronidazole is actively secreted in the saliva where it may be exerting anti-microbial action against dental plaque-bound *H. pylori* colonies that the bismuth compounds administered alone in swallowable tablets cannot reach.

Interestingly, the antibiotics administered as single agents were only partially effective. Even though metronidazole is secreted in the saliva and may eradicate *H. pylori* in the mouth, it is not effective in single-handedly eradicating *H. pylori* in the gastric mucosa, i.e., the stomach. Therefore, assuming this explanation is correct, it is reasonable to believe that in order to achieve nearly complete eradication of *H. pylori,* and prevent relapses of ulcers, it is essential to eradicate the bacterium from the oral cavity, and possibly the throat and esophagus, as well as from the gastric mucosa.

However, it was not known whether bismuth compounds would be therapeutically effective in the oral cavity. In prior use of CBS against ulcers, it was known that CBS undergoes conversion to bismuth trioxide under the influence of gastric acids in the stomach. Conventional wisdom accepted that bismuth trioxide was the active product in the eradication of duodenal *H. pylori.* Therefore, it was not expected that CBS in a chewing gum would show efficacy in eradicating *H. pylori* in the mouth. Moreover, it was not known at what dose levels bismuth compounds would provide therapeutic effectiveness, if at all, for topical use in the mouth.

Chewing gum formulations in this invention have since been shown to be therapeutically effective in clinical studies. Preferably, the chewing gum releases enough bismuth into saliva for eradication of *H. pylori* in the oral cavity. The minimum inhibitory concentration (MIC) of bismuth for *H. pylori* varies for each bismuth compound. For instance, it is established that the MIC of CBS for *H. pylori* is 8 $\mu$g/mL, and its range is 4 to 32 $\mu$g/mL.

Therefore, to ensure its effectiveness, the chewing gum formulation preferably releases bismuth into saliva up to at least 2 times the MIC, preferably a minimum of 2 to 10 times the MIC, most preferably 2 to 250 times the MIC. To achieve these concentrations in the saliva, the bismuth content per dosage of chewing gum can be between about 3.5 mg and about 75 mg, preferably between about 3.5 mg and about 37 mg, more preferably between about 9 mg and about 28 mg. The amount of bismuth-containing compound per dosage thus is determined by the bismuth content of that particular compound. For instance, each piece of CBS-containing chewing gum may contain between about 10 mg and about 200 mg of CBS, preferably between about 10 mg and about 100 mg, and more preferably between about 25 mg and about 75 mg. Accordingly, each piece of gum may include amounts of other bismuth compounds that provide the same bismuth equivalent as the aforementioned ranges of CBS.

Of course, the amount of bismuth compound in each piece may be halved so that a person would chew on two pieces at a time to have the same effective amount of bismuth. Also, the chewing gum should be chewed multiple times throughout the day to prevent the *H. pylori* colonies from returning to their original size. Preferably, the chewing gum will be administered in sequential doses of between one and ten times per day, more preferably between two and six times per day. Also, the chewing gum administered may comprise an active pharmaceutical agent that consists essentially of a bismuth compound selected from the group consisting of colloidal bismuth subcitrate (CBS), bismuth citrate, bismuth subcitrate, bismuth salicylate, bismuth subsalicylate, bismuth subnitrate, bismuth subcarbonate, bismuth tartrate, bismuth subgallate, and bismuth aluminate and combinations thereof.

In another embodiment of the present invention, the chewing gum containing a previously described bismuth compound is administered simultaneously (or concomitantly) with a peroral dosage form, such as a swallowable tablet, containing a previously described bismuth compound.

The bismuth content of the chewing gum used for the concomitant treatment of the present invention may be the same as that of the chewing gum that is administered by itself. The bismuth content of the swallowable tablet can be equivalent to between about 300 mg–1200 mg of colloidal bismuth subcitrate per day, preferably. The concomitant treatment can be administered once or twice per day, more preferably once per day.

A wide range of changes and modifications to the embodiments of the invention described above will be apparent to persons skilled in the art. The following examples are not to be construed as imposing limitations on the invention, but are included merely to illustrate preferred embodiments.

EXAMPLE 1

Preparation of Active Agent

To an aqueous solution of ammonia are added bismuth citrate, citric acid, and caustic potash in specific stoichiometric proportions, and at specific temperatures. The solution is examined for turbidity and, if required, additional volume of ammonia solution is added to render the solution clear. The solution is then filtered on a carbon bed and spray dried to obtain free-flowing powder material. The product is packaged in an air and moisture proof glass container.

EXAMPLE 2

Preparation of Chewing Gum

A brief general description of the chewing gum is set forth as follows. Fully melt the gum base (at approximately 90° C.) in Bartender mixer, a jacketed mixer with sigma blades. Remove the hot water from the mixer jacket, allow to cool, and add lecithin and mix well. Cool further to approximately 50° C., and add liquid flavor and mannitol. Mix until uniform. Dry blend colloidal bismuth subcitrate in sorbitol, and blend sodium citrate in sorbo syrup. Add sorbitol and sorbo syrup blends to the gum base. Cool the product to 35° C., add flavor and sweetener and mix until smooth. Remove the product from the mixing kettle, roll to form a sheet of uniform thickness and score to produce chewing gum sticks weighing 2.5 g each. Wrap individual gum sticks in aluminum foil and place in plastic bags.

EXAMPLE 3

Composition of CBS-Containing Gum

Two variations of 50 mg CBS gum were prepared as shown in Table 1 below. Both formulations used were identical with the exception that Formula-2 contained sodium citrate to impart a firmer texture, while Formula-1 did not.

TABLE 1

FORMULATIONS OF THE GUM (APPROX. 2.5 gm A PIECE)

| Formula-1 | | Formula-2 | |
|---|---|---|---|
| CBS | 50.0 mg | CBS | 50.0 mg |
| Crystalline Sorbitol | 910.0 | Crystalline Sorbitol | 910.0 |
| Gum Base | 575.0 | Gum Base | 575.0 |
| Sorbitol Solution | 500.0 | Sorbitol Solution | 500.0 |
| Mannitol | 400.0 | Mannitol | 400.0 |
| Peppermint Oil | 25.0 | Peppermint Oil | 25.0 |
| Spray Dried Peppermint | 12.5 | Spray Dried Peppermint | 12.5 |
| Grade t Lecithin | 10.0 | Grade t Lecithin | 10.0 |
| Aspartame | 10.0 | Aspartame | 10.0 |
| Sodium Citrate | 10.0 | Total: | 2492.5 mg |
| Total: | 2502.5 mg | | |

EXAMPLE 4

Measurement of Release Rate of Bismuth into Saliva

Among six healthy human subjects, who gave informed consent, three chewed the CBS-containing gum with sodium citrate, and the other three chewed CBS-containing gum without sodium citrate. The subjects chewed the gum samples for a total of 15 minutes. Saliva samples were collected at time interval of 0, 1, 5, 10, and 15 minutes of chewing. The saliva samples were then submitted to an analytical laboratory for bismuth analysis. Results are shown in Table 2 below.

Saliva samples were analyzed for elemental bismuth in ppm units. The results were then converted to μg of active CBS per mL of saliva, and also expressed as a multiple of minimum inhibitory concentration (MIC) of CBS for *H. pylori*. As can be seen from the results for formula-2, the salivary concentrations of CBS are about 156, 64, 5, and 1.8 times the MIC at 1, 5, 10 and 15 minutes, respectively. The constant bathing of the oral cavity from saliva containing sufficient concentration of CBS (2 to 5 times the MIC) for up to 15 minutes can be expected to further reduce the population of viable cells of *H. pylori*.

EXAMPLE 5

Sensory Analysis of Chewing Gum

Sensory characteristics of the chewing gum were evaluated by the subjects during the 15 minutes of chewing. Again, three subjects chewed the CBS gum containing sodium citrate and three subjects chewed the CBS gum without sodium citrate. A nine point rating scale was used to evaluate each category. The results are shown in Tables 3 and 4 below.

TABLE 2

IN VIVO SALIVARY CONCENTRATION OF CBS FROM THE CHEWING GUM

| Formula | chewing time (min.) | saliva vol. (mL) | | conc of Bi (ppm) | | conc of active CBS (μg/mL) | | X MIC | |
|---|---|---|---|---|---|---|---|---|---|
| formula-1 | 0 | 4.4 | (±0.5) | | | | | | |
| | 1 | 3.3 | (±1.4) | 900.7 | (±239.1) | 1270.3 | (±334.7) | 148.7 | (±42.0) |
| | 5 | 5.4 | (±1.5) | 257.7 | (±112.3) | 363.3 | (±158.9) | 45.0 | (±19.9) |
| | 10 | 4.9 | (±1.3) | 28.0 | (±5.0) | 40.0 | (±6.6) | 5.0 | (±1.0) |
| | 15 | 5.2 | (±2.1) | 15.8 | (±17.8) | 25.7 | (±23.0) | 3.1 | (±2.7) |
| formula-2 | 0 | 7.2 | (±0.5) | | | | | | |
| | 1 | 4.8 | (±1.9) | 888.3 | (±329.5) | 1257.0 | (±464.5) | 156.3 | (±58.0) |
| | 5 | 8.5 | (±1.7) | 326.0 | (±113.3) | 572.7 | (±159.7) | 63.7 | (±19.9) |
| | 10 | 7.5 | (±3.4) | 30.0 | (±9.5) | 42.3 | (±13.6) | 5.0 | (±1.7) |
| | 15 | 7.7 | (±3.8) | 10.7 | (±6.7) | 14.7 | (±9.2) | 1.8 | (±1.2) |

TABLE 3

RESULTS OF SENSORY ANALYSIS RATING OF CBS GUM
WITHOUT SODIUM CITRATE
(Formula-1)

| SENSORY CHARACTERISTICS | CHEWING TIME | | | |
|---|---|---|---|---|
| | 1 MIN | 5 MIN | 10 MIN | 15 MIN |
| Overall Flavor | 6.3 | 6.0 | 5.3 | 5.0 |
| (0 = dislike extremely, | (±1.2) | (±1.0) | (±1.5) | (±1.0) |
| 8 = like extremely) | | | | |
| Flavor Intensity | 5.7 | 4.7 | 3.7 | 3.0 |
| (0 = none, 8 = very strong) | (±1.5) | (±1.2) | (±0.6) | (±1.0) |
| Chew Qualities | 6.0 | 6.0 | 5.3 | 5.0 |
| (0 = dislike extremely, | (±1.0) | (±1.0) | (±1.5) | (±1.0) |
| 8 = like extremely) | | | | |
| Unpleasant Aftertaste | 0.0 | 0.0 | 0.0 | 0.0 |
| (0 = none, 8 = very strong) | (±0.0) | (±0.0) | (±0.0) | (±0.0) |
| Overall Qualities | 6.3 | 6.0 | 5.7 | 5.3 |
| (0 = dislike extremely, | (±1.2) | (±1.0) | (±1.2) | (±1.5) |
| 8 = like extremely) | | | | |

TABLE 4

RESULTS OF SENSORY ANALYSIS RATING OF CBS GUM
WITH SODIUM CITRATE
(Formula-2)

| SENSORY CHARACTERISTICS | CHEWING TIME | | | |
|---|---|---|---|---|
| | 1 MIN | 5 MIN | 10 MIN | 15 MIN |
| Overall Flavor | 6.7 | 5.7 | 4.7 | 4.7 |
| (0 = dislike extremely, | (±0.6) | (±1.5) | (±1.2) | (±1.2) |
| 8 = like extremely) | | | | |
| Flavor Intensity | 6.7 | 6.0 | 5.0 | 3.7 |
| (0 = none, 8 = very strong) | (±0.6) | (±0.0) | (±1.0) | (±1.5) |
| Chew Qualities | 4.7 | 5.0 | 4.3 | 4.3 |
| (0 = dislike extremely, | (±2.1) | (±2.0) | (±1.5) | (±0.6) |
| 8 = like extremely) | | | | |
| Unpleasant Aftertaste | 0.7 | 1.7 | 1.7 | 2.0 |
| (0 = none, 8 = very strong) | (±1.2) | (±2.1) | (±2.1) | (±2.0) |
| Overall Qualities | 6.3 | 5.7 | 4.7 | 4.0 |
| (0 = dislike extremely, | (±0.6) | (±1.2) | (±1.2) | (±1.0) |
| 8 = like extremely) | | | | |

In general there were no dramatic differences in the sensory analysis between the two formulas. The sensory panel clearly shows that both chewing gum formulations have a desirable level of flavor and taste, and cause a minimal unpleasant aftertaste after chewing.

EXAMPLE 6

Topical Safety

Topical safety was evaluated in the six volunteers for up to 60 minutes after administration of the gum. The subjects were asked to report any adverse effects such as discomfort or irritation in the oral cavity.

There were no reports of any discomfort or irritation in the oral cavity by any of the subjects at either the 15 or 60 minute post administration time periods.

EXAMPLE 7

Storage Stability Study

Samples of chewing gum containing 50 mg of CBS were wrapped individually in foil wrappers. The pieces of gum were then placed in foil laminate bags, sealed, and placed in storage. Storage conditions include 40° C. and room temperature (RT). The duration of the stability testing was 90 days. The results are shown in Tables 5–8 below.

TABLE 5

THREE MONTH STABILITY DATA
IN VIVO SALIVARY CONCENTRATIONS IN HUMAN SUBJECTS
OF CBS FROM THE 50 MG CBS CHEWING GUM

| TIME/ CONDITION | CHEWING TIME (min) | SALIVA VOLUME (mL) | CONC OF Bi (ppm) | CONC OF Bi ($\mu$g/mL) | CONC OF ACTIVE CBS ($\mu$g/mL) | X MIC |
|---|---|---|---|---|---|---|
| ZERO TIME | 0 | 4.2 (±1.6) | NA | NA | NA | NA |
| | 1 | 4.9 (±4.5) | 1937.3 (±753.5) | 1937.3 (±753.5) | 2729.0 (±1060.2) | 341.0 (±132.7) |
| | 5 | 6.4 (±3.1) | 437.0 (±152.1) | 437.0 (±152.1) | 615.7 (±214.5) | 77.0 (±26.9) |
| | 10 | 3.9 (±0.1) | 36.0 (±28.6) | 36.0 (±28.6) | 50.7 (±40.5) | 6.4 (±5.0) |
| | 15 | 4.5 (±1.3) | 5.0 (±4.6) | 5.0 (±4.6) | 7.0 (±6.6) | 0.9 (±0.8) |
| 3 MONTHS AT 40° C. | 0 | 5.6 (±1.4) | NA | NA | NA | NA |
| | 1 | 2.9 (±1.8) | 1922.3 (±511.8) | 1922.3 (±511.8) | 2710.0 (±791.9) | 338.6 (±96.3) |
| | 5 | 5.6 (±1.7) | 399.3 (±278.1) | 363.7 (±113.3) | 563.0 (±329.3) | 70.3 (±49.1) |
| | 10 | 5.3 (±1.4) | 25.7 (±11.4) | 30.0 (±9.5) | 362.0 (±160.5) | 45.4 (±20.1) |
| | 15 | 4.9 (±0.4) | 7.9 (±4.9) | 10.7 (±6.7) | 10.8 (±6.8) | 1.4 (±0.9) |
| 3 MONTHS AT ROOM TEMP. | 0 | 5.1 (±1.3) | NA | NA | NA | NA |
| | 1 | 4.1 (±1.5) | 1240.0 (±458.7) | 1240.0 (±458.7) | 1748.0 (±646.6) | 218.0 (±80.6) |
| | 5 | 7.2 (±2.3) | 518.7 (±118.7) | 518.7 (±118.7) | 731.3 (±167.6) | 91.0 (±21.8) |
| | 10 | 6.0 (±2.2) | 12.5 (±10.6) | 12.5 (±10.6) | 17.7 (±14.6) | 2.1 (±1.8) |
| | 15 | 5.6 (±1.6) | 4.5 (±2.2) | 4.5 (±2.2) | 6.0 (±2.6) | 0.7 (±0.3) | n = 3 for each group

TABLE 6

THREE MONTH STABILITY DATA
RESULTS OF SENSORY ANALYSIS RATING OF 50 MG CBS GUM

| | SENSORY | CHEWING TIME | | | |
|---|---|---|---|---|---|
| | CHARACTERISTIC | 1 MIN | 5 MIN | 10 MIN | 15 MIN |
| ZERO TIME | OVERALL FLAVOR | 6.7 (±0.6) | 6.3 (±0.6) | 5.3 (±0.6) | 5.3 (±0.6) |
| | FLAVOR INTENSITY | 6.3 (±1.2) | 5.3 (±1.2) | 4.0 (±1.0) | 4.0 (±1.0) |
| | CHEW QUALITIES | 6.7 (±0.6) | 6.3 (±0.6) | 5.7 (±0.6) | 5.3 (±0.6) |
| | UNPLEASANT AFTERTASTE | 0.0 (±0.0) | 0.0 (±0.0) | 0.0 (±2.1) | 0.0 (±0.0) |
| | OVERALL QUALITIES | 6.7 (±0.6) | 6.3 (±0.6) | 5.7 (±0.6) | 5.3 (±1.2) |
| 3 MONTHS AT | OVERALL FLAVOR | 6.0 (±0.0) | 4.7 (±0.6) | 2.7 (±1.2) | 2.7 (±1.2) |
| 40° C. | FLAVOR INTENSITY | 5.3 (±1.2) | 3.0 (±0.0) | 2.3 (±0.6) | 2.0 (±1.0) |
| | CHEW QUALITIES | 5.7 (±0.6) | 5.0 (±1.0) | 4.3 (±0.6) | 4.3 (±0.6) |
| | UNPLEASANT AFTERTASTE | 0.3 (±0.6) | 0.3 (±0.6) | 0.0 (±0.0) | 0.0 (±0.0) |
| | OVERALL QUALITIES | 6.0 (±0.0) | 4.3 (±0.6) | 2.7 (±0.6) | 2.3 (±0.6) |
| 3 MONTHS AT | OVERALL FLAVOR | 6.3 (±0.6) | 6.3 (±0.6) | 5.3 (±0.6) | 4.3 (±0.6) |
| ROOM TEMP. | FLAVOR INTENSITY | 5.7 (±1.5) | 5.3 (±1.5) | 4.3 (±1.5) | 4.0 (±1.7) |
| | CHEW QUALITIES | 6.0 (±1.0) | 6.0 (±1.0) | 5.3 (±0.6) | 4.3 (±0.6) |
| | UNPLEASANT AFTERTASTE | 0.0 (±0.0) | 0.0 (±0.0) | 0.0 (±0.0) | 0.0 (±0.0) |
| | OVERALL QUALITIES | 6.3 (±0.6) | 6.3 (±0.6) | 5.3 (±0.6) | 4.7 (±1.2) |

Note: n = 3 for each analysis
Rating Scale:
0 = dislike extremely, 9 - like extremely for: Overall Flavor, Chew Quality, Overall Quality
0 = none, 9 - like extremely for: Flavor Intensity
0 = none, 9 = very strong for: Unpleasant Aftertaste

TABLE 7

EXPONENTIAL REGRESSION DATA OF TIME VS SALIVARY CONCENTRATIONS EXPRESSED AS MULTIPLES OF MIC

| | Initial Test Lot | Stability Lot #CBS-50CG-0002 | | | Clinical Lot |
|---|---|---|---|---|---|
| | #CBS-50-CG-0001 | Zero Time | 3 mo./RT | 3 mo./40° C. | #CBS-50CG-0003 |
| A (intercept) | 240.0 | 563.1 | 575.7 | 422.3 | 446.5 |
| b (slope) | −0.339 | −0.432 | −0.361 | −0.448 | −0.426 |
| r (correlation coefficient) | 0.992 | 0.998 | 0.948 | 0.971 | 0.959 |
| K (pseudo first order rate constant) | −0.339 | 0.432 | 0.361 | 0.448 | 0.426 |
| $t_{0.5}$ (min.) | 2.04 | 1.60 | 1.92 | 1.55 | 1.63 |

Mean $t_{0.5}$ = 1.748 (±0.218)

TABLE 8

RELEASE OF CBS FROM THE CHEWING GUM AFTER 15 MINUTES OF CHEWING BY HUMAN SUBJECTS

| | Stability Lot #CBS-50CG-0002 | | | Clinical Lot |
|---|---|---|---|---|
| | Zero Time | 3 mo./RT | 3 mo./40° C. | #CBS-50CG-0003 |
| Mg CBS/2.5 g gum Before chewing (%) | 45.6 (100) | 44.5 (100) | 46.1 (100) | 46.2 (100) |
| Mg CBS/2.5 g gum After 15 min chewing (%) | 3.5 (7.6) | 4.0 (9.0) | 4.5 (9.8) | 3.8 (8.5) |

Mean % of CBS Remaining in the gum after 15 min of chewing = 8.6 (±1.0)

Each piece of the gum used for the stability study (one for zero-time, two for three months, total three) was from the same lot number. The results show that bismuth concentration remains stable over the tested time period.

EXAMPLE 8

Denture Material Exposure Study

An evaluation of CBS salivary concentration on various denture materials was conducted in order to test any potential staining effect of the CBS on denture materials. Artificial saliva was used. The results are reported at Table 9 below.

TABLE 9

THE COMPOSITION OF ARTIFICIAL SALIVA

| Ingredients | Concentration per Liter |
| --- | --- |
| Sodium Bicarbonate | 0.50 g |
| Sodium Phosphate, Dibasic, Dihydrate | 0.85 g |
| Calcium Chloride | 0.44 g |
| Magnesium Chloride | 0.06 g |
| Potassium Chloride | 1.40 g |
| Sodium Carboxyl Methyl Cellulose | 2.00 g |
| Phosphoric Acid to adjust pH to 6.4 Distilled Water | QS |

The test saliva was prepared by dissolving 0.500 g of colloidal bismuth subcitrate in 100 mL of the above artificial saliva. 500 mL of artificial saliva at room temperature was placed in one of two identical glass jars with lids. In the other jar was placed 500 mL of the artificial saliva at room temperature containing 0.50% of CBS. In each of the jars the denture material block and a magnetic stirrer was placed. The jars were then placed on the magnetic platform and set to agitate at a minimum rate for four hours. The denture materials that were exposed to artificial saliva containing either CBS or placebo are listed in Table 10 below.

The four hour exposure of natural tooth and other denture materials to 0.5% CBS in artificial saliva with mild agitation did not cause any staining, discoloration, or changes in texture.

TABLE 10

DENTURE MATERIALS

1) Natural tooth with silver amalgam filling
2) Composite resin (used on anterior teeth for filling)
3) Denture base acrylic resin
4) Porcelain fused to metal
5) Partial denture metal frame
6) Acrylic tooth (artificial)
7) Natural tooth

EXAMPLE 9

Clinical Efficacy Data

An open label, placebo-controlled pilot clinical study in ten patients with initial positive response for *H. pylori* in the dental plaque has been initiated. Data from six patients (four patients treated with CBS 50 mg chewing gum six times-a-day and two patients treated with placebo chewing gum six times-a-day for fifteen days) has been obtained. The dental plaque samples from the patients were collected before treatment, at day 7 and at day 15 after treatment, and tested by microbiological culture and CLO test. The results are set forth in Table 11 below:

TABLE 11

| | CLO | DUR POSITIVE (HRS:MINS) | CULTURE | SIDE EFFECTS (Stain/Odor) |
| --- | --- | --- | --- | --- |
| TREATED GROUP (n = 4) | | | | |
| Pt 1 Day 0 | + | 1:00 | + | NE |
| 30/M Day 7 | + | 1:45 | -ve | — |
| Day 15 | + | 1:30 | -ve | — |
| Pt 2 Day 0 | + | 2:15 | + | NE |
| 42/M Day 7 | + | 1:30 | NA | — |
| Day 15 | + | 4:00 | -ve | — |
| Pt 3 Day 0 | + | 2:30 | + | NIL |
| 31/M Day 7 | + | 4:30 | NA | NIL |
| Day 15 | + | 5:30 | NA | NIL |
| Pt 4 Day 0 | + | 2:30 | NA | NIL |
| 29/F Day 7 | + | 4:00 | NA | NIL |
| Day 15 | + | 5:30 | NA | NIL |
| Mean CLO response time after 15 days = 4.125 HR | | | | |
| PLACEBO (n = 2) | | | | |
| Pt 1 Day 0 | + | 1:00 | NA | NIL |
| 26/M Day 7 | + | 1:30 | NA | NIL |
| Day 15 | + | 1:30 | NA | NIL |
| Pt 2 Day 0 | + | 1:15 | NA | NIL |
| 28/M Day 7 | + | 2:00 | NA | NIL |
| Day 15 | + | 2:30 | NA | NIL |
| Mean CLO response time after 15 days = 2.0 HR | | | | |

NA = Not available
NE = Not evaluated (before chewing)

The data show that for patients treated with CBS 50 mg chewing gum and placebo chewing gum on day 15 the mean CLO response times are 4.125 hours and 2.0 hours, respectively. The longer CLO test response time for CBS 50 mg chewing gum group compared to the placebo chewing gum group is indicative of substantial reduction in *H. pylori* density in the oral cavity of the active treatment group.

EXAMPLE 10

Clinical Trial Data

The MERETEK UBT™ (urea breath test kit) from MERETEK Diagnostics, Inc. can be used to detect the presence of *H. pylori* in the stomach for the diagnosis of ulcers. To perform the test, the patient is given a liquid containing urea that is enriched with the carbon-13 isotope. *H. pylori* is a urease positive bacteria. If the carbon-13 isotope is present in heavy concentrations in later breaths, it signifies the presence of *H. pylori* in the stomach.

Duodenal ulcer patients with a positive urea breath test were randomized into active and placebo groups and entered into a 15-day clinical trial. These patients did not receive any antibiotic therapy during the clinical trial. The patients in the active group received gum containing 50 mg of colloidal bismuth subcitrate per piece. The patients in the placebo group received gum not containing colloidal bismuth subcitrate. The patients were further subdivided into high dose and low dose groups. The patients in the high dose group chewed gum 6 times per day and the patients in the low dose group chewed gum 2 times per day. After 15 days, the urea breath test was repeated. The results are reported in Table 12 below.

TABLE 12

UREA BREATH TEST RESULTS FROM 15-DAY CLINICAL TRIAL

| Subject Initials | Subject Group | Overall Assessment (Initial) | Overall Assessment* (Day 15) | Overall Change in Data** (Initial to Day 15) | |
|---|---|---|---|---|---|
| A | high active | + | + | decrease | 79% |
| B | high active | + | − | decrease | 86% |
| C | high active | + | − | decrease | 93% |
| D | high active | + | − | decrease | 89% |
| E | high active | + | − | decrease | 98% |
| F | high active | + | − | decrease | 98% |
| G | low active | + | + | decrease | 22% |
| H | low active | + | + | decrease | 24% |
| I | low active | + | − | decrease | 98% |
| J | low active | − | − | decrease | 51% |
| K | low active | + | − | decrease | 94% |
| L | low active | + | − | decrease | 95% |
| M | high placebo | + | + | increase | 42% |
| N | low placebo | + | + | increase | 35% |
| O | low placebo | + | + | decrease | 9% |

*Overall assessment is a qualitative result (either positive or negative) based on a numerical value established for the test.
**Overall change in data refers to the difference in numerical values from initial test to day 15.

Results of Overall Assessment:
1. All three patients receiving placebo (100%) had positive urea breath tests at the conclusion of the trial.
2. Eight of eleven patients receiving active gum (73%) had negative urea breath tests at the conclusion of the trial.
3. One patient with negative results at the start (i.e., below threshold value to consider the test positive) was not included.

Results of Overall Changes in Data:
1. The average change in urea breath test data was an increase of 23% in the three placebo patients.
2. The average change in urea breath test data was a decrease of 64% in the six patients on the low active dose (range of 22% to 98%).
3. Six of six patients in the low active drug group had a decrease (p<0.05 by chi-square analysis).
4. The average change in urea breath test data was a decrease of 91% in the six patients on the high active dose (range of 79% to 98%).
5. Six of six patients in the high active drug group had a decrease (p<0.05 by chi-square analysis).

Summary of Results:
1. Twelve of twelve patients on active gum had decreases in urea breath test data results (ranging from 22% to 98%), whereas three placebo patients had an average increase of 23%).
2. There was a dose-response relationship between the two doses of gum used. The data suggest that the doses are near the peak of the dose-response relationship.
3. The data strongly suggest that *H. pylori* has been eradicated from the stomach by the active gum used in this clinical trial.

EXAMPLE 11

Antibacterial Efficacy for Treatment of Halitosis

Halitosis is caused by the buildup of Volatile Sulfur Compounds (VSC's). These VSCs arise from the breakdown of bacteria, tissue, and food particles trapped in the mouth. Other contributing factors include digestive problems, nose, throat and/or lung infections, and the intake of medications.

A halitosis meter can be used to detect the presence of bad breath. This meter uses an analyzer that can detect the levels of VSCs. Most individuals feel that odor is coming from their stomach, when really 80 percent originates from the mouth and tongue.

Typically, breath mints, chewing gum, mouth washes and toothpastes that you buy at the store merely mask your bad breath. These breath fresheners are only able to cover up the odor for a short time. In order to permanently eliminate bad breath it is necessary to attack the source of the VSCs.

Campylobacter rectus, Helicobacter pylori, and Treponema denticola are bacteria that have been demonstrated to be associated with Halitosis (bad breath). The bismuth-containing compounds and methods of the present invention, including CBS as well as ascorbyl bismuth derivative, have demonstrated in vitro activity against all three bacteria, as indicated by their minimum effective concentrations (MICs) presented in Table 13 below.

TABLE 13

| Test Organisms | Bismuth Ascorbyl Sulfate ($\mu$g/ml) | Bismuth Sucrose Sulfate ($\mu$g/ml) | CBS ($\mu$g/ml) |
|---|---|---|---|
| *Campylobacter rectus* | 256 | >256 | 256 |
| *Helicobacter pylori* | 8 | 16 | 2 |
| *Treponema denticola* | 16 | 32 | 32 |

Based on the in vitro activity, a chewing gum containing CBS should be effective in reducing Halitosis caused by bacteria. It is expected that a person may treat halitosis by chewing gum containing preferably between about 10 mg CBS and about 100 mg CBS, and preferably between about one and four times per day. Also, the chewing gum may contain an amount of bismuth in the aforementioned bismuth compound or combinations thereof equivalent to between about 10 and about 100 milligrams of colloidal bismuth subcitrate.

EXAMPLE 12

Toxicology

A number of animal toxicity studies and human clinical investigations have demonstrated safety of bismuth compounds, especially CBS, in therapeutic dose ranges. No toxicity has been reported in chronic daily administration of high doses of CBS (160, 320, and 640 mg/kg body weight representing 2, 4, and 8 times the human therapeutic dose, respectively) in rats treated for three months or dogs treated for six months. See Wieriks et al., Journal of Gastroenterology 17 (Supplement 80): 11B16 (1982), incorporated herein by reference.

Long term safety of CBS and treatment of peptic ulcers at a standard dose of 480 mg (expressed as bismuthtrioxide) in four daily divided doses has been examined by Bader, Digestion 37 (Supplement 2): 53–59 (1987), incorporated herein by reference. CBS was first introduced in Europe in 1971 and since that time 1.5 million treatments have been dispensed. During eight years of use of CBS tablets [De-Nol®] in Europe between 1978 and 1986 under a more comprehensive adverse reaction monitoring system, only 13 adverse reaction forms were completed. Five of these adverse reactions were ascribed to CBS: one case of headache, one case of stomach pain, one case of diarrhea, and two cases of allergy (mainly in the form of skin rashes). A high degree of safety of CBS in therapeutic applications for the treatment of peptic ulcers is reported in a review of pharmacology of bismuth-containing compounds by Lambert, Review of Infectious Diseases 13 (Supplement 8): 691–695 (1991), incorporated herein by reference. In reviewing safety and pharmacokinetics of CBS, Bennet, Scandinavian Journal of Gastroenterology 26 (Supplement 185): 29–35 (1991), incorporated herein by reference, has calculated the systemic bioavailability of bismuth after oral dosing of CBS to be in the range of 0.16 to 0.28% of the administered dose, and concluded that steady-state blood levels of 50–100 ng/mL are unlikely to cause any neurotoxicity.

It should be appreciated that the compositions and methods of the present invention are capable of being incorporated in the form of a variety of embodiments, only a few of which have been illustrated and described above. The invention may be embodied in other forms without departing from spirit or essential characteristics. The described embodiments are to be considered in all respects only as illustrative and not restrictive, and the scope of the invention is, therefore, indicated by the appended claims rather that the foregoing description. All changes which come within the meaning and range of equivalency of the claims are to be embraced within their scope.

What is claimed is:

1. A chewing gum composition comprising a water soluble bulk portion, a water insoluble chewing gum base portion, a flavoring agent, and a therapeutically effective amount of a compound, a non-H-2 antagonist selected from the group consisting of colloidal bismuth subcitrate, bismuth subcitrate, bismuth citrate, bismuth salicylate, bismuth subsalicylate, bismuth subnitrate, bismuth subcarbonate, bismuth tartrate, bismuth subgallate, bismuth aluminate, and combinations thereof.

2. The chewing gum of claim 1 wherein the bismuth compound is selected from the group consisting of colloidal bismuth subcitrate, bismuth subcitrate, bismuth subsalicylate and combinations thereof.

3. The chewing gum of claim 2 wherein the bismuth compound is colloidal bismuth subcitrate.

4. The chewing gum of claim 3 wherein the chewing gum includes between about 10 mg and 200 mg of colloidal bismuth subcitrate per piece.

5. The chewing gum of claim 4 wherein the chewing gum includes between about 10 mg and about 100 mg of colloidal bismuth subcitrate per piece.

6. The chewing gum of claim 5 wherein the chewing gum includes between about 25 mg and 75 mg of colloidal bismuth subcitrate per piece.

7. The chewing gum of claim 1 further comprising an antibiotic.

8. The chewing gum of claim 7 wherein the antibiotic is metronidazole.

9. The chewing gum of claim 1 further comprising an anti-plaque agent.

10. The chewing gum of claim 9 wherein said antiplaque agent is selected from gluconase and hydroglucosidase, glucose oxidase, calcium kaolin, silicone oil, and sanguinarine.

11. A chewing gum formulation comprising a bismuth compound, a non-H-2 antagonist selected from the group consisting of colloidal bismuth subcitrate (CBS), bismuth citrate, bismuth subcitrate, bismuth salicylate, bismuth subsalicylate, bismuth subnitrate, bismuth subcarbonate, bismuth tartrate, bismuth subgallate, and bismuth aluminate.

12. The chewing gum of claim 11 wherein the chewing gum includes an amount of bismuth in said bismuth compound or combinations thereof equivalent to between about 10 and about 200 milligrams of colloidal bismuth subcitrate.

13. The chewing gum of claim 12 wherein the chewing gum includes an amount of bismuth in said bismuth compound or combinations thereof equivalent to between about 25 and about 75 milligrams of colloidal bismuth subcitrate.

14. The chewing gum of claim 13 wherein the chewing gum includes an amount of bismuth in said bismuth compound or combinations thereof equivalent to about 50 milligrams of colloidal bismuth subcitrate.

15. A method of treating *Helicobacter pylori* infection comprising the step of administering a chewing gum containing a water soluble bulk portion, a water insoluble chewing gum base portion, a flavoring agent, and a therapeutically effective amount of a compound, a non-H-2 antagonist selected from the group consisting of colloidal bismuth subcitrate, bismuth subcitrate, bismuth citrate, bismuth salicylate, bismuth subsalicylate, bismuth subnitrate, bismuth subcarbonate, bismuth tartrate, bismuth subgallate, bismuth aluminate and combinations thereof.

16. The method of claim 15 wherein said bismuth compound is selected from the group consisting of colloidal bismuth subcitrate, bismuth subcitrate, bismuth subsalicylate, and a combination thereof.

17. The method of claim 16 wherein the bismuth compound is colloidal bismuth subcitrate.

18. The method of claim 17 wherein the chewing gum includes between about 10 mg and 200 mg of colloidal bismuth subcitrate.

19. The methd of claim 18 wherein the chewing gum includes between about 10 mg and about 100 mg of colloidal bismuth subcitrate per piece.

20. The chewing gum of claim 19 wherein the chewing gum includes between about 25 mg and about 75 mg of colloidal bismuth subcitrate per piece.

21. The method of claim 15 wherein the chewing gum further comprises an antiplaque agent.

22. The method of claim 15 wherein the chewing gum is administered between about one and ten times per day.

23. A method of treating Helicobacter pylori infection comprising the step of administering a chewing gum containing a therapeutically effective amount of a bismuth compound, a non-H-2 antagonist selected from the group consisting of colloidal bismuth subcitrate, bismuth subcitrate, bismuth citrate, bismuth salicylate, bismuth subsalicylate, bismuth subnitrate, bismuth subcarbonate, bismuth tartrate, bismuth subgallate, bismuth aluminate and combinations thereof.

24. The method of claim 23 wherein the chewing gum includes an amount of bismuth in said bismuth compound or combinations thereof equivalent to between about 10 and about 200 milligrams of colloidal bismuth subcitrate.

25. The method of claim 24 wherein the chewing gum includes an amount of bismuth in said bismuth compound or combinations thereof equivalent to between about 25 and about 75 milligrams of colloidal bismuth subcitrate.

26. The method of claim 25 wherein the chewing gum includes an amount of bismuth in said bismuth compound or combinations thereof equivalent to about 50 milligrams of colloidal bismuth subcitrate.

27. A method for treating halitosis comprising administering a chewing gum containing a water soluble bulk portion, a water insoluble chewing gum base portion, a flavoring agent, and a therapeutically effective amount of a compound, a non-H-2 antagonist selected from the group consisting of colloidal bismuth subcitrate, bismuth subcitrate, bismuth citrate, bismuth salicylate, bismuth subsalicylate, bismuth subnitrate, bismuth subcarbonate, bismuth tartrate, bismuth subgallate, bismuth aluminate and combinations thereof.

28. The method of claim 27 wherein said bismuth compound is selected from the group consisting of colloidal bismuth subcitrate, bismuth subcitrate, bismuth subsalicylate, and combinations thereof.

29. The method of claim 28 wherein the bismuth compound is colloidal bismuth subcitrate.

30. The method of claim 29 wherein the chewing gum is administered between about one and ten times per day.

31. The method of claim 30 wherein the chewing gum is administered between about one and four times per day.

32. The method of claim 27 wherein the chewing gum includes an amount of bismuth in said bismuth compound or combinations thereof equivalent to between about 10 and about 100 milligrams of colloidal bismuth subcitrate.

* * * * *